United States Patent
Lee et al.

(10) Patent No.: US 6,699,892 B2
(45) Date of Patent: Mar. 2, 2004

(54) PHARMACEUTICALLY ACCEPTABLE SALT OF AMLODIPINE AND METHOD OF PREPARING THE SAME

(75) Inventors: Fang Yu Lee, Taichung (TW); Tsang-Miao Huang, Chunghua (TW); Chao-Ho Chung, Hsinchu (TW)

(73) Assignee: Yung Shin Pharmaceutical Industrial Co., Ltd., Taichung (TW)

( * ) Notice: Subject to any disclaimer, the term of this patent is extended or adjusted under 35 U.S.C. 154(b) by 0 days.

(21) Appl. No.: 10/160,154

(22) Filed: Jun. 4, 2002

(65) Prior Publication Data
US 2003/0225143 A1 Dec. 4, 2003

(51) Int. Cl.[7] ................. A61K 31/44; C07D 213/79
(52) U.S. Cl. ............................. 514/356; 546/263
(58) Field of Search ..................... 514/356; 546/263

(56) References Cited

U.S. PATENT DOCUMENTS

| | | |
|---|---|---|
| 4,572,909 A | 2/1986 | Campbell et al. |
| 4,806,557 A | 2/1989 | Campbell et al. |
| 4,879,303 A | 11/1989 | Davison et al. |
| 4,971,984 A | 11/1990 | Frigerio et al. |
| 5,250,548 A | 10/1993 | Winn et al. |
| 5,438,145 A | 8/1995 | Furlan et al. |
| 6,046,337 A | 4/2000 | Bozsing et al. |
| 6,262,092 B1 | 7/2001 | Chang et al. |
| 6,265,417 B1 | 7/2001 | Carroll et al. |

*Primary Examiner*—Raymond Henley, III
(74) *Attorney, Agent, or Firm*—Fei-Fei Chao, Ph.D.; Venable LLP

(57) ABSTRACT

The present invention discloses a novel and improved pharmaceutical salt, nicotinate, of amlodipine having the following formula:

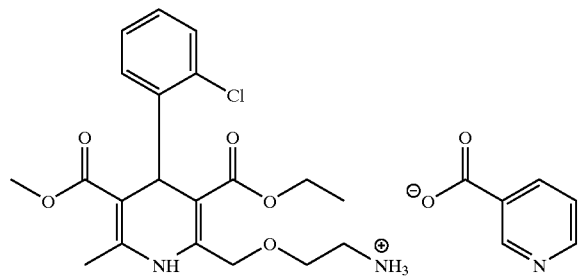

The present invention also discloses methods for preparing and using the same.

19 Claims, No Drawings

PHARMACEUTICALLY ACCEPTABLE SALT OF AMLODIPINE AND METHOD OF PREPARING THE SAME

FIELD OF THE INVENTION

The present invention relates to a pharmaceutical composition containing the nicotinate salt of amlodipine. The pharmaceutical composition can be used as an antihypertensive or antiischemic agent. The present invention also relates to a method of preparing the pharmaceutical composition.

BACKGROUND OF THE INVENTION

The compound amlodipine, which has the generic name of 3-ethyl 5-methyl ±2-[(2-aminoethoxy)methyl]-4-(2-chlorophenyl)-1,4-dihydro-6-methyl-3,5-pyridine dicarboxylate, was first disclosed in EP-B1-0 089 167 as a new substance and a useful anti-ischaemic and anti-hypertensive agent. Amlodipine is sold in tablet form by Pfizer Inc. under the tradename NORVASC®, and in capsule form by Novartis under the tradename LOTREL.

Amlodipine belongs to a class of dihydropyridines (DHP). This class of DHP is generally referred to as calcium channel blockers or calcium antagonists. They act to reduce the movement of calcium into the cell and are thus able to delay or prevent the cardiac contracture, which is caused by an accumulation of intracellular calcium under ischemic conditions. Excessive calcium influx during ischemia can have a number of additional adverse effects that would further compromise the ischemic myocardium. These include less efficient use of oxygen for ATP production, activation of mitochondrial fatty acid oxidation and, possibly, promotion of cell necrosis. Thus calcium antagonists are useful in the treatment or prevention of a variety of cardiac conditions, such as angina pectoris, cardiac arrythmias, heart attacks and cardiac hypertrophy. Calcium antagonists also have vasodilator activity since they can inhibit calcium influx in cells of vascular tissue and are thus also useful as antihypertensive agents and for the treatment of coronary vasospasm.

Though effective as a free base, amlodipine is best known to be administered as pharmaceutically acceptable acid addition salts. For example, U.S. Pat. No. 4,572,909 discloses the pharmaceutically acceptable acid addition salts of amlodipine as those formed from acids which form non-toxic acid addition salts containing pharmaceutically acceptable anions, such as the hydrochloride, hydrobromide, sulphate, phosphate or acid phosphate, acetate, maleate, fumarate, lactate, tartrate, citrate and gluconate salts. The maleate salt being presented as the most preferred compound.

U.S. Pat. No. 4,879,303 discloses several improved pharmaceutical salts of amlodipine, including mesylate, besylate, tosylate, succinate, and salicylate. In particular, the besylate salt of amlodipine is described as the most preferred compound which demonstrates improved solubility, stability, non-hygroscopicity and processability. Amlodipine besylate is prepared by reacting free base amlodipine with benzene-sulphonic acid or ammonium benzenesulphonate in an inert solvent such as industrial methanol at the temperature of 5° C.

U.S. Pat. No. 4,806,557 discloses certain DPHs which are pro-drugs of amlodipine and intermediates useful in the preparation of these pro-drugs. The pharmaceutically acceptable salts of these pro-drugs include hydrochloride, hydrobromide, sulphate or bisulphate, phosphate or acid phosphate, acetate, citrate, fumarate, gluconate, lactate, maleate, succinate, tartrate, methanesulphonate (also known as mesylate), benzenesulphonate (also known as besylate) and p-toluenesulphonate (also known as tosylate) salts.

U.S. Pat. No. 5,438,145 discloses a process for the preparation of amlodipine besylate which is different from that described in U.S. Pat. No. 4,879,303. The process described in U.S. Pat. No. 5,438,145 includes the reaction of amlodipine and benzenesulphonic acid in methanolic or aqueous methanolic medium at a temperature from 20° C. to the reflux temperature.

U.S. Pat. No. 6,046,337 discloses yet another process of preparing amlodipine besylate which, according to the patentees, has the advantage of carrying out the process in a simple way, achieving high yields, and not having to isolate the amlodipine base.

In the invention to be presented in the following sections, a novel and improved pharmaceutically acceptable salt form of amlodipine is described. The preferred pharmaceutically acceptable salt is nicotinate. Nicotinate is the salt form of nicotinic acid, an essential water soluble vitamin which is best known for its effect on pellagra and as a component of NADP and NAD. The nicotinate salt of amlodipine demonstrates stability, non-hygroscopicity and processability similar to those of amlodipine besylate. The solubility of amlodipine nicotinate is far better than that of amlodipine besylate.

SUMMARY OF THE INVENTION

The present invention provides a pharmaceutical compound which contains a nicotinate salt of a dihydropyridine (DHP) class calcium channel blocker drug. Optionally, the pharmaceutical compound is in admixture with excipients. The preferred DHP class calcium channel blocker is amlodipine. The preferred amlodipine nicotinate contains amlodipine and nicotinate at a molar ratio of about 1:1. The solubility (in water at room temperature) of the nicotinate salt of amlodipine is more than 2 mg/ml, preferably at about 6 mg/ml. The pH value of the nicotinate salt of amlodipine is at about 5.0 and 6.0. A pharmaceutical composition of the present invention containing the nicotinate salt of a DHP class calcium channel blocker can be in the form of tablets, capsules, and/or sterile aqueous solutions.

The present invention also provides a method for preparing the pharmaceutical compound, which includes the steps of: (1) dissolving a free base amlodipine in a lower alkyl alcohol to form an amlodipine solution; (2) adding nicotic acid to the amlodipine solution to form the amlodipine nicotinate mixture; and (3) slowly cooling down the amlodipine nicotinate mixture to 0° C. to form the pharmaceutical compound.

The lower alkyl alcohol used for solubilizing the free base amlodipine includes, but is not limited to, methanol, ethanol, propanol, isopropanol, butanol, isobutanol, pentanol, and isopentanol. The preferred lower alkyl alcohol is ethanol. It is preferred to disslove the free base amlodipine in ethanol with heat (at 30° C.—the reflux temp of selected solvent) and stirring. After the addition of the nicotinate to the dissolved amlodipine solution, the amlodipine nicotinate mixture is gradually cooled down to 0° C. in about 1 hour.

The amlodipine nicotinate mixture is further purified by filtration using conventional method(s) and commercially available filtration device or filters. The filtered amlopidine nicotinate is further washed with ethyl acetate and dried under reduced pressure (at 25° C. and 760 mm-Hg).

The pharmaceutical composition of the present invention is suitable for use as an antihypertensive or antiischaemic agent. It can be used to treat patients with hypertension or ischaemia by orally or intraperitoneally administering an effective amount of the pharmaceutical composition to patients.

DETAILED DESCRIPTION OF THE INVENTION

There are three major classes of calcium channel blockers, which are (1) dihydropyridine (such as nifedipine), (2) phenylalkamine (such as verapamil), and (3) benzothiazapine (such as diltiazem). Amlopidine belongs to the dihydropyridine (DHP) class of calcium channel blockers. Other DHP includes nifedipine, nicardipine (Cardene®), nimodipine, nitrendipine (Nitrepin®), nisoldipine (Sula®), felodipine, isradipine (DynaCirc®), lacidipine, lercanidipine, benidipine (Coniel®), vatanidipine, and pranidipine.

The amlodipine nicotinate of the present invention has a chemical structure as shown below:

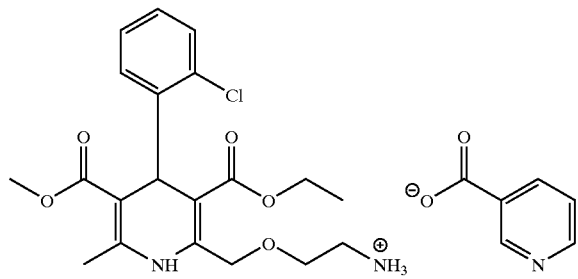

which is structurally and physically distinctive from the currently available besylate (also known as benzenesulphonate) salt of amlopidipine. See Table 1 infra.

The nicotinate salt of amlodipine of the present invention was prepared by first placing the amlodipine free base in ethanol or an aqueous ethanolic mixture. The ethanol mixture was then heated with stirring until the solid was completely dissolved. Nicotinic acid was added to the resultant solution and the mixture was slowly cooled down to 0° C. for about 1 hour. The solids formed were collected by filtration, and further washed with ethyl acetate. The final product of the present invention was obtained by drying under reduced pressure.

The following example is illustrative, but not limiting the scope of the present invention. Reasonable variations, such as those occur to reasonable artisan, can be made herein without departing from the scope of the present invention.

EXAMPLE 1

Preparation of Nicotinate Salt of Amlodipine

The pharmaceutical composition of the present invention was prepared as follows:

Amlodipine free base (4.09 g) was added to 40 mL of ethanol. The mixture was heated at reflux and stirred until the solid was completely dissolved. Nicotinic acid (1.23 g) was added to the amlodipine solution and then the mixture was slowly cooled down to 0° C. within one hour. The solids formed were isolated by filtration, washed with ethyl acetate and dried under reduced pressure to yield 4.51 g of amlodipine nicotinate.

The molar ratio of amlodipine free base to nicotinic acid added was 1:1.008.

EXAMPLE 2

Identification of Nicotinate Salt of Amlodipine

The nicotinate salt of amlodipine of present invention was identified using the proton ($^1$H) and carbon-13 ($^{13}$C) nuclear magnetic resonance (NMR) spectroscopy. The $^1$H-NMR chemical shifts of the chemical in deuterated chloroform (CDCl$_3$-d) are tabulated in Table 1:

TABLE 1

Identification of Nicotinate Salt of Amlodipine by Proton ($^1$H) and Carbon-13 ($^{13}$C) Nuclear Magnetic Resonance (NMR) Spectroscopy

| Chemical Shift (ppm) | Multiplicity | Functional Group | |
|---|---|---|---|
| 1.08 | Triplet | —OCH$_2$C$\underline{H_3}$ | J = 7.1 |
| 2.13 | Singlet | —CH$_3$ | |
| 3.14 | Multiplet | —OCH$_2$C$\underline{H_2}$NH$_2$ | |
| 3.49 | Singlet | —OCH$_3$ | |
| 3.70 | Multiplet | —OC$\underline{H_2}$CH$_2$NH$_2$ | |
| 3.93 | Multiplet | —OC$\underline{H_2}$CH$_3$ | |
| 4.61 | Quartet | —C—CH$_2$—O | J = 9.2 |
| 5.52 | Singlet | —C—C—H | |
| 6.62–7.24 | Multiplet | —Ar—H, 8H | |
| 7.78 | Singlet | —NH | |
| 8.14–8.50 | double duplet | —NH$_2$ | J = 68 Hz, J = 36 Hz |
| 9.10 | Singlet | —NH | |

The $^{13}$C NMR chemical shifts of the chemical in deuterated chloroform (CDCl$_3$-d) are at 14.16; 18.77; 37.27; 39.71; 50.68; 59.90; 67.98; 76.99; 102.61; 103.42; 123.30; 126.82; 127.37; 129.25; 131.14; 131.39; 132.33; 137.35; 144.34; 144.70; 145.62; 150.41; 151.11; 167.22; 167.99; and 171.10 ppm.

EXAMPLE 3

Comparison Between Amlodipine Nicotinate and Amlodipine Besylate

Amlodipine nicotinate was compared to amlodipine besylate in Table 2 as shown below:

TABLE 2

Comparative Studies Between Amlodipine Nicotinate and Amlodipine Besylate

| | pH Value | Stability Test (% of Sample Purity) (3-week) | | Solubility in Water at Room Temperature (mg/ml) |
|---|---|---|---|---|
| | | 45° C. | 75° C. | |
| Amlodipine Besylate | 6.09 | 99.6 | 97.8 | 2.0 |
| Amlodipine Nicotinate | 5.34 | 99.7 | 99.2 | 6.0 |

As shown in Table 2, the aqueous solution of amlodipine nicotinate had a pH value of 5.34. In comparison, the pH value of the aqueous solution of amlodipine besylate was 6.09.

Amlodipine nicotinate also showed improved water solubility over amlodipine besylate. At the ambient temperature (room temperature of about 25° C.), a saturated aqueous solution of amlodipine nicotinate contains about 6.0 mg of the chemical per mL of water. In comparison, a saturated aqueous solution of amlodipine besylate contains about 2.0 mg of the chemical per mL of water.

The stability of amlodipine nicotinate and amlodipine besylate was tested at 45° C. and 75° C. for 3 weeks. As shown in Table 2, at 45° C., the stability of amlodipine nicotinate was similar to that of amlodipine besylate, both showed about 100% unchanged rates (99.7% vs. 99.6%, respectively). However, at 75° C., amlodipine nicotinate demonstrated better stability than amlodipine besylate (99.2% vs. 97.8%, respectively).

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A pharmaceutical compound comprising a nicotinate salt of a dihydropyridine (DHP) class calcium channel blocker.

2. A pharmaceutical composition, comprising said pharmaceutical compound according to claim 1 and at least one excipient.

3. The pharmaceutical compound according to claim 1, wherein said DHP class calcium channel blocker is amlodipine.

4. The pharmaceutical compound according to claim 3, wherein said nicotinate salt of amlodipine has a solubility of more than 2 mg/ml in water at room temperature.

5. The pharmaceutical compound according to claim 4, wherein said nicotinate salt of amlodipine has a solubility of about 6 mg/ml in water at room temperature.

6. The pharmaceutical compound according to claim 3, wherein said nicotinate salt of amlodipine is at pH between 5.0 and 6.0.

7. The pharmaceutical composition according to claim 2, wherein said pharmaceutical composition is in a form of a tablet, a capsule, or a sterile aqueous solution.

8. A method for preparing the pharmaceutical compound according to claim 3, comprising:

dissolving a free base amlodipine in a lower alkyl alcohol to form an amlodipine solution;

adding nicotinate to the amlodipine solution to form the amlodipine nicotinate mixture; and slowly cooling down the amlodipine nicotinate mixture to 0° C. to form the pharmaceutical compound.

9. The method according to claim 8, wherein said lower alkyl alcohol is at least one selected from the group consisting of methanol, ethanol, propanol, isopropanol, butanol, isobutanol, pentanol and isopentanol.

10. The method according to claim 8, wherein said lower alkyl alcohol is ethanol.

11. The method according to claim 10, wherein said amlodipine solution is dissolved in ethanol with heat and stirring.

12. The method according to claim 8, wherein said amlodipine nicotinate mixture is cooled down to 0° C. for a duration of about 1 hour.

13. The method according to claim 8, wherein said pharmaceutical compound is further purified by filtration.

14. The method according to claim 13, wherein said filtered pharmaceutical compound is further washed with ethyl acetate.

15. The method according to claim 14, wherein said ethyl acetate-washed pharmaceutical compound is further dried under reduced pressure.

16. An antihypertensive agent comprising the pharmaceutical compound according to claim 1.

17. An antiischemic agent comprising the pharmaceutical compound according to claim 1.

18. A method for treating hypertension in patients suffering therefrom comprising administering an effective amount of the pharmaceutical composition according to claim 2 to said patients.

19. A method for treating ischemia in patients suffering therefrom comprising administering an effective amount of the pharmaceutical composition according to claim 2 to said patients.

* * * * *